United States Patent [19]

Isomura et al.

[11] Patent Number: 5,013,725

[45] Date of Patent: * May 7, 1991

[54] PHARMACEUTICAL COMPOSITIONS SUBSTITUTED AMINOMETHYLENEBIS(PHOSPHONIC ACID) DERIVATIVES

[76] Inventors: Yasuo Isomura, 4-12-11-919, Tabata sukai Haitsu, Nishiogu, Arakawa-ku, Tokyo, Japan, 116; Makoto Takeuchi, 3-63-16, Purejiru Enomoto 201, Higashioizumi, Nerima-ku, Tokyo, Japan, 178; Shuichi Sakamoto, 3-17-7, 402, Sakae-cho, Higashimurayama-shi, Tokyo, Japan, 189; Tetsushi Abe, 7-8-9, Azuma-cho, Iruma-shi, Saitama, Japan, 358

[ * ] Notice: The portion of the term of this patent subsequent to Jun. 12, 1990 has been disclaimed.

[21] Appl. No.: 495,388

[22] Filed: Mar. 16, 1990

Related U.S. Application Data

[62] Division of Ser. No. 333,971, Apr. 5, 1989, Pat. No. 4,933,472.

[30] Foreign Application Priority Data

| Apr. 8, 1988 | [JP] | Japan | 63-86347 |
| Apr. 11, 1988 | [JP] | Japan | 63-89632 |
| Feb. 18, 1989 | [JP] | Japan | 1-38871 |

[51] Int. Cl.$^5$ ................. A61K 31/66; A61K 31/665; A61K 31/67
[52] U.S. Cl. ........................ 514/99; 514/95; 514/102
[58] Field of Search ............... 514/95, 99, 102

[56] References Cited

U.S. PATENT DOCUMENTS 4,933,472  6/1990  Isomura et al. .................. 549/218

FOREIGN PATENT DOCUMENTS 54-37829  3/1979  Japan.

Primary Examiner—Richard L. Raymond
Attorney, Agent, or Firm—Burgess, Ryan & Wayne

[57] ABSTRACT

Substituted aminomethylenebis(phosphonic acid) derivatives represented by the general formula:

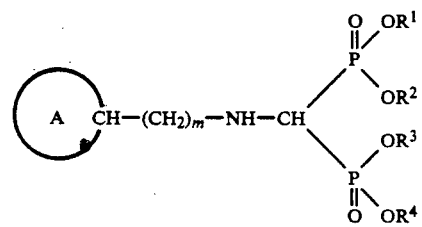

in which $R^1$, $R^2$, $R^3$ and $R^4$ may be the same or different, each represents a hydrogen atom or a lower alkyl group; "m" is zero or represents an integer from 1 to 4; and a ring "A" represents a cycloalkenyl group having 5 to 8 carbon atoms, a bicycloheptyl group, a bicycloheptenyl group or a saturated heterocyclic group having 4 to 7 carbon atoms and containing an oxygen atom, a sulfur atom, a sulfinyl group (—SO—) or a sulfonyl group (—SO$_2$—), or pharmaceutically acceptable salts thereof.

4 Claims, No Drawings

PHARMACEUTICAL COMPOSITIONS SUBSTITUTED AMINOMETHYLENEBIS(PHOSPHONIC ACID) DERIVATIVES

This is a division, of application Ser. No. 333,971, filed Apr. 5, 1989, now U.S. Pat. No. 4,933,472.

BACKGROUND OF THE INVENTION

1. Field of the Invention

The present invention relates to substituted aminomethylenebis(phosphonic acid) derivatives or pharmaceutically acceptable salts thereof which are useful as medicines having a bone resorption inhibitory effect as well as an anti-inflammatory effect, an antirheumatic effect or the like.

2. Description of the related art

Substituted aminomethylenebis(phosphonic acid) derivatives having a heterocyclic ring are disclosed in Japanese patent laid-open No. 89,293/1980. The compounds disclosed in this Japanese patent gazette have an isoxazolyl group or a pyrazolyl group as the heterocyclic ring. The Japanese patent gazette mentions that these compounds can be used as agricultural chemicals, especially as herbicide, but is quite silent on the usability of the compounds as medicines.

Japanese patent laid-open No. 150,290/1988 also discloses derivatives having a heterocyclic aryl ring composed of five atoms and Japanese patent laid-open No. 210,033/1986 discloses derivatives having a nitrogen-containing heterocyclic aromatic ring composed of six atoms. These Japanese patent gazettes mention that these compounds have a bone resorption inhibitory effect. However, no compound who's hetero ring is a saturated hetero ring has been reported.

Another type of substituted aminomethylenebis(phosphonic acid) derivatives having a cycloaliphatic hydrocarbon group is also known. Japanese patent laid-open No. 37,829/1979 discloses compounds having an unsubstituted cyclopentyl group or a cyclohexyl group as the cycloaliphatic hydrocarbon group and Japanese patent publication No. 12319/1980 also discloses compounds having a cyclohexyl group as the cycloaliphatic hydrocarbon group. These Japanese patent gazettes mention that these compounds can be used as agricultural chemicals, especially as herbicide and that they can be used in a method for preventing precipitation in water or in aqueous solution, but are quite silent on the usability of the compounds as medicines.

However, such compounds that have a bicycloheptyl group, a bicycloheptenyl group or a cycloalkenyl group as the cycloaliphatic hydrocarbone group are not known.

SUMMARY OF THE INVENTION

The present invention provides (saturated heterocyclic ring substituted)aminomethylenebis(phosphonic acid) derivatives having the general formula (I):

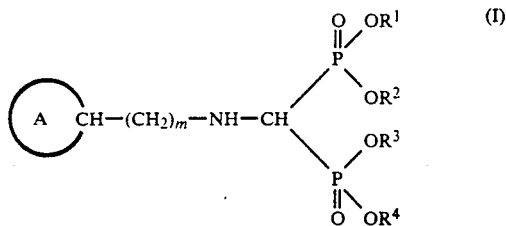

in which $R^1$, $R^2$, $R^3$ and $R^4$ may be the same or different, each represents a hydrogen atom or a lower alkyl group; "m" is zero or represents an integer from 1 to 4; and a ring "A" represents a cycloalkenyl group having 5 to 8 carbon atoms, a bicycloheptyl group, a bicycloheptenyl group or a saturated heterocyclic group having 4 to 7 carbon atoms and containing an oxygen atom, a sulfur atom, a sulfinyl group (—SO—) or a sulfonyl group (—SO$_2$—), or pharmaceutically acceptable salts thereof.

In the definition of the groups in the general formulae in the present specification, the term "lower" means a linear or branched carbon chain having 1 to 5 carbon atoms, if they are not mentioned otherwise. Therefore, the "lower alkyl group" may be methyl group, ethyl group, propyl group, isopropyl group, butyl group, isobutyl group, sec-butyl group, tert-butyl group, pentyl(amyl) group, iso-pentyl group, neo-pentyl group or the like.

The "saturated hetero ring group" represented by a chemical structure:

in the general formula (I) means a saturated alicyclic group having 4 to 7 carbon atoms any one of which is replaced by an oxygen atom, a sulfur atom, a sulfinyl group (—SO—) or a sulfonyl group (—SO$_2$—) and may be 2- or 3-tetrahydrofufuryl group, 2-, or 3-tetrahydrothiophenyl group, 2-tetrahydropyranyl group, 3-tetrahydropyranyl group, 4-tetrahydropyranyl group, 2-tetrahydrothiopyranyl group, 4-tetrahydrothiopyranyl group, 1-oxidotetrahydro-2-thiopyranyl group, 1-oxidotetrahydro-4-thiopyranyl group, 1,1-dioxidotetrahydro-3-thiopyranyl group or 1,1-dioxidotetrahydro-4-thiopyranyl group or the like.

As the "bicycloheptyl group", there may be mentioned 2-bicyclo[2.2.1]heptyl group, 7-bicyclo[2.2.1]heptyl group, 3-bicyclo[3.2.0]heptyl group, 3-bicyclo[3.1.1]heptyl group or 4-bicyclo[4.1.0]heptyl group or the like. As the "bicycloheptenyl group", there may be mentioned 7-bicyclo[2.2.1]-2-heptenyl group, 3-bicyclo[3.2.0]-6-heptenyl group, 4-bicyclo[3.1.1]-2-heptenyl group or the like.

As the "cycloalkenyl group having 5 to 8 carbon atoms", there may be mentioned 2- or 3-cyclopentenyl group, 2- or 3-cyclohexenyl group, 2-, 3-, or 4-cycloheptenyl group, 2-, 3- or 4-octenyl group or the like.

The compounds according to the present invention include tetraesters of which $R^1$ to $R^4$ are lower alkyl groups or monoesters, diesters and triesters of which one to three of $R^1$ to $R^4$ is a lower alkyl group or are lower alkyl groups.

The compounds form salts when they are free phosphonic acids. The objective compounds of the present invention may be pharmaceutically acceptable salts of the compounds (I). As preferable salts, it can be mentioned salts with inorganic bases such as salts with alkali metal, for example, sodium salts, potassium salts and salts with alkali earth metal, for example, calcium salts or magnesium salts; salts with organic bases such as ammonium salts, methylamine salts, ethylamine salts, dimethylamine salts, diethylamine salts, trimethylamine salts, triethylamine salts, cyclohexylamine salts, ethanolamine salts or diethanolamine salts; salts with basic amino acid such as lysine salts or ornithine salts or the like.

The compounds of the present invention may have asymmetric carbon atoms. Thus, the compounds of the present invention include all the isomers based on the asymmetric carbon atoms such as optical isomers and racemic compounds.

PREPARING METHODS OF THE COMPOUNDS

The compounds (I) of the present invention can be prepared by the following three reaction routes:

First Method:

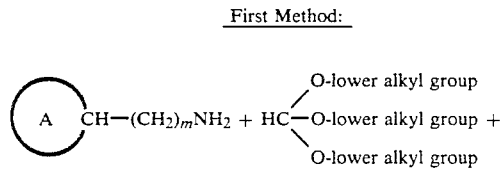

(II)    (III)

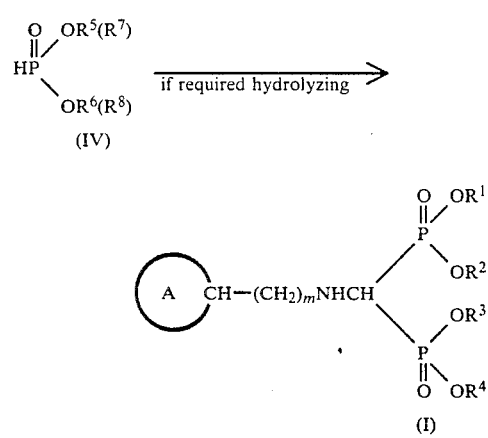

Second Method:

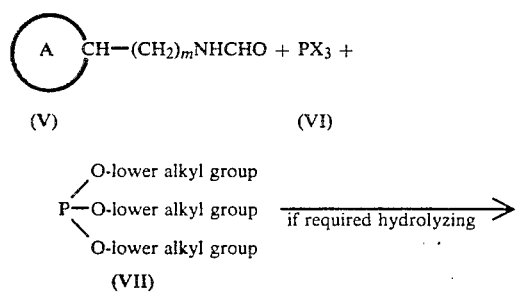

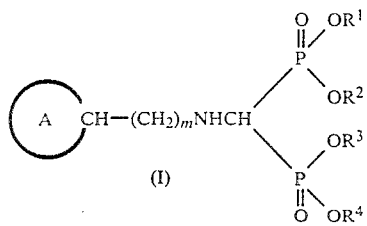

(I)

Third Method:

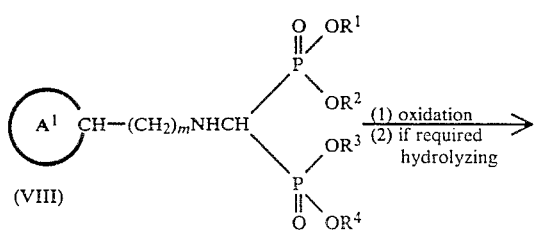

(VIII)  (1) oxidation
        (2) if required hydrolyzing

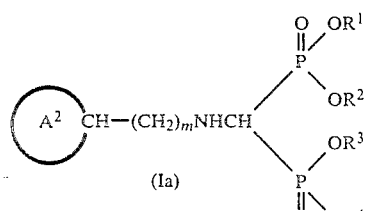

(Ia)

in which "$A^1$" represents a saturated hetero ring having 4 to 7 carbon atoms and containing a sulfur atom or a sulfinyl group (—SO—), "$A^2$" represents a saturated hetero ring having 4 to 7 carbon atoms and containing a sulfinyl group (—SO—) or a sulfonyl group (—$SO_2$—), "X" represents a halogen atom and $R^5$, $R^6$, $R^7$ and $R^8$ represent a lower alkyl group respectively. Now, we will describe each of these three routes in more details.

First Method

In this method, all components of an aminoalkyl saturated heterocyclic compound (II), a lower alkyl orthoformate (III) and a phosphite (IV) are mixed each in the stoichiometric amount and are heated to effect reaction. A reaction solvent is not specifically required. The reaction is carried out at 100° to 200° C., preferably at 150° C. or so for several ten minutes to several hours.

For isolating and purifying the thus obtained reaction product, the reaction mixture is passed through a silica gel column and is eluted with a mixed solvent of methanol-chloroform.

In the reaction of the aminoalkyl saturated heterocyclic compound (II) with the lower alkyl orthoformate (III), an intermediate of iminoether represented by the general formula:

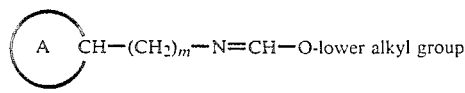

can be isolated.

This intermediate of iminoether is then reacted with the phosphite (IV) to give the compound (I). The thus obtained bisphosphonates can be converted optionally into the corresponding bisphosphonic acids by hydrolysis. The hydrolysis is generally carried out by heating the bisphosphonates under reflux in concentrated hydrochloric acid. Alternatively, the hydrolysis can be effected by treating the bisphosphonates with a strong acid or a trimethylsilyl halide in a waterfree solvent. For the method, in general, a commercial anhydrous hydrobromic acid in acetic acid can be used directly or in a form of a pertinently diluted solution, or a solution of a trimethylsilyl iodide as dissolved in a solvent such as carbon tetrachloride, dimethylformamide, chloroform, toluene or the like can be used. Regarding the temperature, the hydrolysis is carried out with cooling or heating. For example, when the ester is hydrolyzed with a trimethylsilyl halide with cooling at $-10°$ C. or lower, a partially hydrolyzed product is obtained.

Second Method

In this method, a mixed solution of phosphorous trihalogenide (VI) and trialkyl phosphite (VII) is reacted at first at 40° to 100° C., preferably at 60° to 80° C. for 15 to 30 minutes. After formylamino compound (VIII) is added to the resulting solution, the mixed solution is heated at 40° to 100° C., preferably at 60° to 80° C. for several hours. The progress of the reaction can easily be confirmed by TLC (thin layer chromatography, with a developer system of chloroform-methanol). After the completion of the reaction, the excess trialkyl phosphite is removed by distillation. As the halogen atoms, there may be mentioned chlorine atom, bromine atom or iodine atom.

For isolation and purification of the thus obtained reaction product, the reaction mixture is directly passed through a silica gel column chromatography, or alternatively is dissolved in chloroform and is washed with water and, after the solvent is distilled off, the resulting residue is purified by a silica gel column chromatography.

Third Method

This method is effected by oxidizing the compound represented by the general formula (VIII) and then optionally hydrolyzing the oxidized compound.

The oxidation can be carried out by any method which can convert sulfide group (—S—) or sulfinly group (—SO—) into a sulfinyl group (—SO—) or a sulfonyl group (—$SO_2$—). For exmple, the oxidation can be effected by treating the compound (VIII) with potassium permanganate, chromic acid, hydrogen peroxide or organic peracids such as peracetic acid, perbenzoic acid, methachloroperbenzoic acid or the like.

The reaction solvent can be chosen among acetone, acetonitrile, dioxane, benzene, dichloromethane, chloroform or the like. The compound thus obtained can be optionally hydrolyzed by the method described in the First method to give the compound (Ia) of the present invention.

When the bisphosphonic acids are converted into their salts, the acids are treated with a base such as sodium hydroxide, potassium hydroxide, ammonia, organic amine or the like by usual methods.

The isolation and purification of the objective product (I) can be carried out by usual chemical treatments such as extraction, crystallization, a variety of chromatographic operations or the like.

The compounds (I) and their salts provided by the present invention have a bone resorption-inhibitory action and also have an action for inhibiting hypercalcemia caused by bone resorption. In addition, these are recognized to have excellent anti-inflammatory action and analgesic action.

Experimental test methods and results will be described hereunder so as to support the inhibitory effect on hypercalcemia of the compounds (I) and their salts provided by the present invention.

Inhibitory Effect on Hypercalcemia

Rats of hypercalcemia induced by administration of parathyroid hormone were used and the decrement of the serum calcium amount by administration of the compound was measured.

Test Method

Human 1-34 parathyroid hormone (PTH, manufactured by Peptide Laboratory) which was dissolved in a 0.1% BSA (bovine serum albumin)-containing physiological saline was intravenously injected in an amount of 30 μg/kg (5 ml/kg as the solution) to 5-week-old male Wistar rats which had been fasting for 20 hours. To a normal control group, 0.1% BSA-containing physiological saline alone was injected in the same manner. 45 minutes after the PTH injection, the rats were etherized and then subjected to celiotomy in order to collect blood from the abdominal cava with a vacuum blood-collecting tube. The blood collected was immediately centrifuged by 3000 rpm at 4° C. for 10 minutes to isolate the serum. The concentration of ionized calcium ($Ca^{++}$) in the serum was immediately measured in a $Ca^{++}$ meter (Sera 250, manufactured by Horiba Manufacturing Co.).

The compounds of the present invention were dissolved in physiological saline and pH was adjusted to 7.4 with sodium hydroxide and hydrochloric acid. The solution was subcutaneously administered at a dose of 2 ml/kg 72 hours before the PTH injection. In the same manner, a physiological saline was administered to the normal control group and the control group.

The results for each group were expressed in terms of mean ±S.E. (standard error) and comparison was made among the groups by testing by one-way analysis of variance. The significance level was taken at 5%.

Results

The results obtained by the subcutaneous and oral administration are shown in Table 1.

TABLE 1

| Subcutaneous and oral administration | | | |
|---|---|---|---|
| Compound Tested | Dose (mg/kg) | N | Serum $Ca^{++}$ (m mole/liter) |
| Normal Control (−PTH) | — | 5 | 1.42 ± 0.02** |
| Control (+PTH) | — | 5 | 1.48 ± 0.02 |
| Compound of Example 3 | 0.1 sc | 5 | 1.27 ± 0.01** |
|  | 0.3 sc | 5 | 1.07 ± 0.02** |
|  | 1.0 sc | 5 | 1.06 ± 0.03** |
| Compound of Example 3 | 10 po | 5 | 1.42 ± 0.02 |
|  | 30 po | 5 | 1.34 ± 0.02** |
|  | 100 po | 5 | 1.06 ± 0.04** |
| Normal Control (−PTH) | — | 5 | 1.42 ± 0.02 |
| Control (+PTH) | — | 5 | 1.48 ± 0.02 |
| Compound of Example 13 | 0.01 sc | 5 | 1.46 ± 0.01 |
|  | 0.03 sc | 5 | 1.42 ± 0.02 |
|  | 0.1 sc | 5 | 1.26 ± 0.01** |
| Compound of Example 13 | 10 po | 5 | 1.49 ± 0.01 |
|  | 30 po | 5 | 1.39 ± 0.03** |
|  | 100 po | 5 | 1.17 ± 0.03** |
| Normal Control (−PTH) | — | 5 | 1.38 ± 0.02** |
| Control (+PTH) | — | 5 | 1.48 ± 0.02 |
| Compound of Example 13 | 0.1 sc | 5 | 1.23 ± 0.02** |
|  | 0.3 sc | 5 | 1.09 ± 0.04** |
|  | 1.0 sc | 5 | 1.03 ± 0.02** |
| Normal Control (−PTH) | — | 5 | 1.41 ± 0.01** |
| Control (+PTH) | — | 5 | 1.54 ± 0.02 |
| Compound of Example 17 | 0.01 sc | 5 | 1.46 ± 0.00** |
|  | 0.03 sc | 5 | 1.35 ± 0.01** |
|  | 0.1 sc | 5 | 1.17 ± 0.02** |

TABLE 1-continued

| Subcutaneous and oral administration | | | | |
|---|---|---|---|---|
| Compound Tested | | Dose (mg/kg) | N | Serum Ca++ (m mole/liter) |
| Normal Control | (−PTH) | — | 5 | 1.42 ± 0.01** |
| Control | (+PTH) | — | 5 | 1.52 ± 0.01 |
| Compound of | | 3 po | 5 | 1.49 ± 0.01 |
| Example 17 | | 10 po | 5 | 1.45 ± 0.02* |
| | | 30 po | 5 | 1.34 ± 0.02** |

Mean value: ±S.E.
*P < 0.05
**P < 0.01

From the test results, the compounds of the present invention were demonstrated to have an excellent action for reducing the amount of serum calcium. Accordingly, it is confirmed that the compounds of the present invention have a boneresorption inhibitory action. As diseases considered to be caused by an excessive boneresorption, there may be mentioned Paget's disease, hypercalcemia, metastatic osteocarcinoma, and osteoporosis. Further, sthenic bone resorption in inflammatory arthritides such as rheumatoid arthritis is also an important problem from a clinical point of view. The compounds provided by the present invention can be used as remedial medicines for these diseases to inhibit the bone resorption and to prevent the reduction of the bone amount or to prevent or reduce the rising of the serum calcium value caused by the sthenic bone resorption.

The compounds (I) of the present invention and their salts can be used as they are or are blended with any pharmaceutically acceptable carrier, vehicle, attenuant or the like to be formed into medical compositions, such as tablets, capsules, powder, granules, pills or the like for oral administration and injection solution, syrup, suppositories, ointment or the like for non-oral administration. The amount of the dose of the compounds (I) of the present invention is, although varying in accordance with the administration route, patient's symptom, etc., generally from 1 mg/day/adult to 1 g/day/adult for oral administration and from 0.1 to 10 mg/day/adult for non-oral administration.

EXAMPLE 1

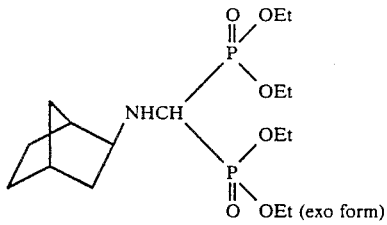

A mixture of 4.0 g of exo-2-aminonorbornane, 6.4 g of ethyl orthoformate and 19.9 g of diethylphosphite was heated at 150° C. for 2 hours under stirring. After cooling, the reaction solution was concentrated under reduced pressure to eliminate diethylphosphite which was not reacted. Then, the residue was purified on silica gel column chromatography (methanol/chloroform=1/99) to give 12.5 g of tetraethyl (2-exo-bicyclo[2.2.1]heptyl)aminomethylenebis(phosphonate) as a pale yellow oil.

The physico-chemical characteristics of this product are as follows:

(i) Mass Spectrum (FAB Mass) 398 (M+ +1)

| (ii) Nuclear Magnetic Resonance Spectrum (δ value, in CDCl₃) | |
|---|---|
| 0.90~1.72 | (20H, CH₃ × 4 and H in methylene at 3, 5, 6, 7 sites in norbornane ring) |
| 2.02~2.32 | (2H, H at 1, 4 sites in norbornane ring) |
| 3.00 | (1H, H at 2 site in norbornane ring) |
| 3.32 | (1H, —NHCH—) |
| 3.96~4.44 | (8H, OCH₂CH₃ × 4) |

In the same manner as Example 1, the following compounds were prepared.

EXAMPLE 2

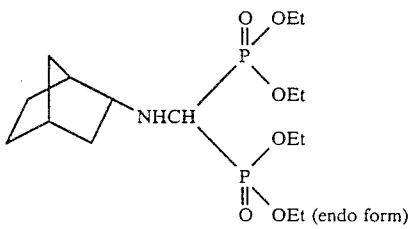

(i) Mass Spectrum (FAB Mass) 398 (M+ +1)

| (ii) Nuclear Magnetic Resonance Spectrum (δ value, in CDCl₃) | |
|---|---|
| 0.60~2.04 | (21H, CH₃ × 4, NH, H in methylene at 3, 5, 6, 7 sites in norbornane ring) |
| 2.08~2.36 | (2H, H at 1, 4 sites in norbornane ring) |
| 3.28 | (1H, NHCH) |
| 3.40 | (1H, H at 2 site in norbornane ring) |

EXAMPLE 3

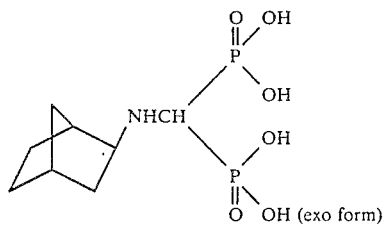

3.0 g of tetraethyl(2-exo-bicyclo[2.2.1]heptyl)aminomethylenebis(phosphonate) was dissolved in 30 ml of concentrated hydrochloric acid and heated under reflux for 3 hours. After cooling, the reaction solution was concentrated under reduced pressure. The obtained residue was precipitated in methanol and then recrystallized from watermethanol (1:1) to give 1.8 g of (2-exo-bicyclo[2.2.1]heptyl)aminomethylenebis(phosphonic acid) as colorless crystals.

The physico-chemical characteristics of this product are as follows:

(i) Mass Spectrum (FAB Mass) 286 (M+ +1)

| (ii) Elemental Analysis (as C₁₈H₁₇NO₆P₂) | | | |
|---|---|---|---|
| | C (%) | H (%) | N (%) |
| Calculated: | 33.69 | 6.01 | 4.91 |
| Found: | 33.43 | 5.86 | 4.93 |

(iii) m.p. (°C.) 231 to 232

In the same manner as Example 3, the following compounds were prepared.

EXAMPLE 4

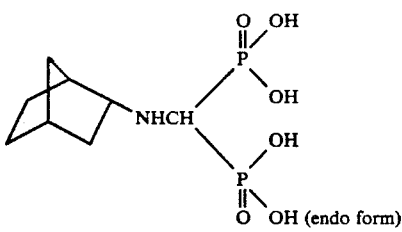

(endo form)

(i) Mass Spectrum (FAB Mass) 286 (M+ +1)

| (ii) Elemental Analysis (as $C_{18}H_{17}NO_6P_2.0.5H_2O$) | | | |
|---|---|---|---|
| | C (%) | H (%) | N (%) |
| Calculated: | 32.66 | 6.17 | 4.76 |
| Found: | 32.52 | 6.04 | 4.77 |

(iii) m.p. (°C.) 237 to 239 (recrystallized from water-methanol)

EXAMPLE 5

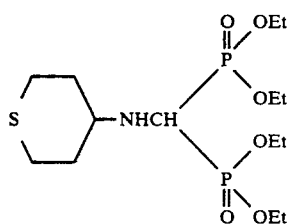

A mixture of 2.6 g of (tetrahydro-2H-thiopyran-4-yl)amine, 4.3 g of ethyl orthoformate and 15.3 g of diethylphosphite was heated at 155° C. under stirring for 3 hours. After cooling, the reaction solution was concentrated under reduced pressure to eliminate diethylphosphite which was not reacted. Then, the residue was purified on a silica gel column chromatography (methanol/chloroform=1/99) to give 6.5 g of tetraethyl (tetrahydro-2H-thiopyran-4-yl)aminomethylenebis(phosphonate) as a pale yellow oil.

The physico-chemical characteristics of this product are as follows:

(i) Mass Spectrum (FAB Mass) 404 (M+ +1)

| (ii) Nuclear Magnetic Resonance Spectrum (δ value, in CDCl₃) | |
|---|---|
| 1.36 | (12H, $-OCH_2C\underline{H}_3 \times 4$) |
| 1.48~2.24 | 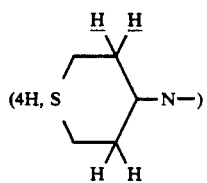 (4H, S) |
| 2.42~3.02 | 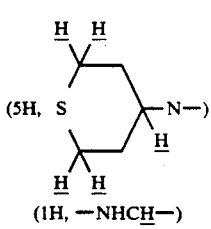 (5H, S) |
| 3.40 | (1H, $-NHC\underline{H}-$) |

| (ii) Nuclear Magnetic Resonance Spectrum (δ value, in CDCl₃) | |
|---|---|
| 4.04~4.40 | (8H, $-OC\underline{H}_2CH_3 \times 4$) |

In the same manner as Example 5, the following compounds were prepared

EXAMPLE 6

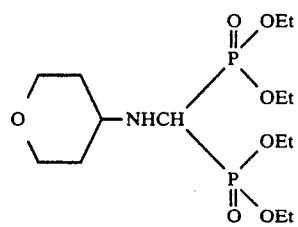

(i) Mass Spectrum (FAB Mass) 388 (M+ +1)

| (ii) Nuclear Magnetic Resonance Spectrum (δ value, in CDCl₃) | |
|---|---|
| 1.34 | (12H, $-OCH_2C\underline{H}_3 \times 4$) |
| 1.40~1.96 | 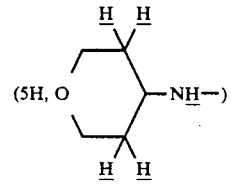 (5H, O) |
| 2.88~3.68 | 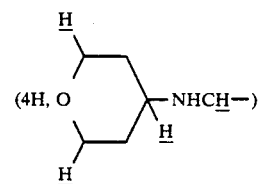 (4H, O) |
| 3.80~4.40 | 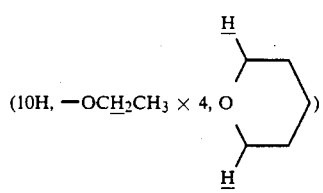 (10H, $-OC\underline{H}_2CH_3 \times 4$, O) |

EXAMPLE 7

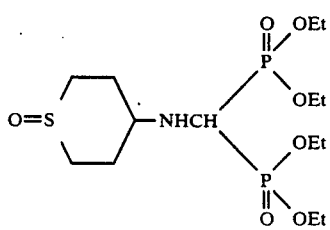

To an ice-cold solution of 1.5 g of tetraethyl (tetrahydro-2H-thiopyran-4-yl)aminomethylenebis(phosphonate) in dichloromethane (15 ml) was added 0.75 g of m-chloroperbenzoic acid and the mixture was stirred for 1 hour.

The reaction solution was washed with saturated aqueous sodium bicarbonate solution and concentrated under reduced pressure. The residue thus obtained was purified on a silica gel column chromatography (methanol/chloroform=1/99) to give 0.68 g of tetraethyl (1-oxidotetrahydro-2H-thiopyran-4-yl)aminomethylenebis(phosphonate) as a pale yellow oil.

The physico-chemical characteristics of this product are as follows:

(i) Mass Spectrum (FAB Mass) 420 ($M^{30}$ +1)

| (ii) Nuclear Magnetic Resonance Spectrum (δ value, in CDCl₃) | |
|---|---|
| 1.36 | (12H, OCH₂C$\underline{H}$₃ × 4) |
| 1.60~2.82 | (7H, O=S ... N$\underline{H}$—) 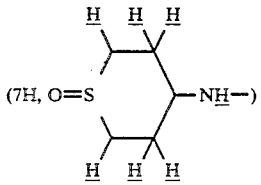 |
| 2.90~3.32 | (3H, O=S ... $\underline{H}$) 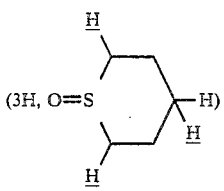 |
| 3.40 | (1H, —NHC$\underline{H}$—) |
| 4.04~4.44 | (8H, OC$\underline{H}$₂CH₃ × 4) |

EXAMPLE 8

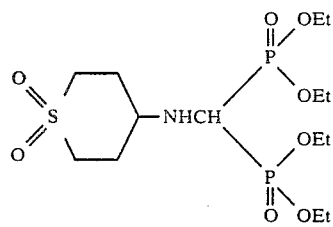

To an ice-cold solution of 1.5 g of tetraethyl (tetrahydro-2H-thiopyran-4-yl)aminomethylenebis(phosphonate) was added 1.5 g of mchloroperbenzoic acid and the mixture was stirred at 35° C. for 2.5 hours. The reaction solution was washed with saturated sodium hydrogen carbonate aqueous solution and concentrated under reduced pressure. The resulting residue was purified on a silica gel column chromatography (methanol/chloroform=1/99) to give 1.55 g of tetraethyl (1,1-dioxidotetrahydro-2H-thiopyran-4-yl)aminomethylenebis(phosphonate) as a colorless oil.

The physico-chemical properties of this product are as follows:

(i) Mass Spectrum (FAB Mass) 436 (M⁺ +1)

| (ii) Nuclear Magnetic Resonance Spectrum (δ value, in CDCl₃) | |
|---|---|
| 1.36 | (12H, OCH₂C$\underline{H}$₃ × 4) |
| 1.60~2.56 | (4H, ...) 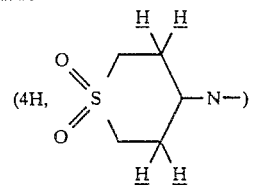 |
| 2.68~3.12 | (3H, ...) 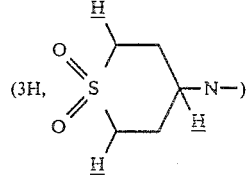 |
| 3.16~3.40 | (3H, ...NHC$\underline{H}$—) 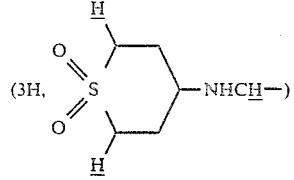 |
| 4.06~4.42 | (8H, OC$\underline{H}$₂CH₃ × 4) |

EXAMPLE 9

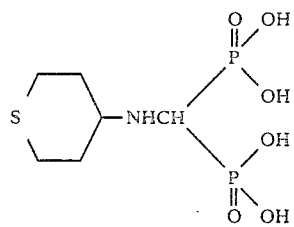

1.7 g of tetraethyl (tetrahydro-2H-thiopyran-4-yl)aminomethylenebis(phosphonate) was dissolved in 20 ml of concentrated hydrochloric acid and heated under reflux for 2.5 hours. After cooling, the reaction solution was concentrated under reduced pressure to eliminate hydrochloric acid, 30 ml of purified water was added to the residue and then the mixture was again concentrated under reduced pressure. The obtained pale yellow solid was recrystallized from water-methanol to give 0.8 g of (tetrahydro-2H-thiopyran-4-yl)aminomethylenebis(phosphonic acid) as colorless crystals in the form of needles.

The pysico-chemical characteristics of this product are as follows:

(i) Mass Spectrum (FAB Mass) 292 (M⁺ +1)

| (ii) Elemental Analysis (as $C_6H_{15}NO_6SP_2$) | | | |
|---|---|---|---|
| | C (%) | H (%) | N (%) |
| Calculated: | 24.75 | 5.19 | 4.81 |
| Found: | 24.95 | 5.16 | 4.71 |

(iii) m.p. (°C.) 235 to 236 (decomposition)

In the same manner as Example 9, the following compounds were prepared.

EXAMPLE 10

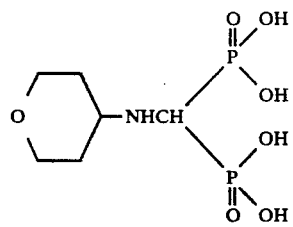

(Tetrahydro-2H-pyran-4-yl)aminomethylenebis(phosphonic acid)

(i) Mass Spectrum (FAB Mass) 276 (M++1)

| (ii) Elemental Analysis (as $C_6H_{15}NO_7P_2$) | | | |
|---|---|---|---|
| | C (%) | H (%) | N (%) |
| Calculated: | 26.19 | 5.50 | 5.09 |
| Found: | 25.99 | 5.29 | 5.06 |

(iii) m.p. (°C.) 231 to 232 (decomposition) (recrystallized from water-methanol)

EXAMPLE 11

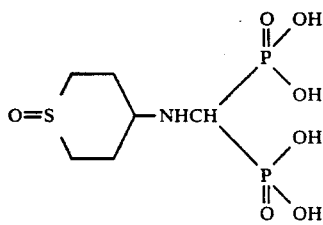

(1-oxidotetrahydro-2H-thiopyran-4-yl)-aminomethylenebis(phosphonic acid)

| (i) Elemental Analysis (as $C_6H_{15}NO_7SP_2$) | | | |
|---|---|---|---|
| | C (%) | H (%) | N (%) |
| Calculated: | 23.46 | 4.92 | 4.56 |
| Found: | 23.47 | 5.02 | 4.68 |

(ii) m.p. (°C.) 222 to 224 (decomposition) (recrystallization from water-methanol)

EXAMPLE 12

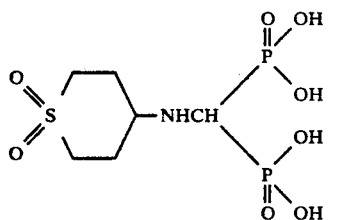

(1,1-dioxidotetrahydro-2H-thiopyran-4-yl)-aminomethylenebis(phosphonic acid)

(i) Mass Spectrum (FAB Mass) 324 (M++1)

| (ii) Elemental Analysis (as $C_6H_{15}NO_8SP_2$) | | | |
|---|---|---|---|
| | C (%) | H (%) | N (%) |
| Calculated: | 22.30 | 4.68 | 4.33 |
| Found: | 22.21 | 4.51 | 4.27 |

(iii) m.p. (°C.) 250 to 253 (decomposition) (recrystallized from water-methanol)

EXAMPLE 13

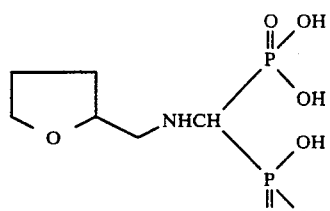

(2,3,4,5-tetrahydro-2-furfuryl)-aminomethylenebis(phosphonic acid)

| (i) Elemental Analysis (as $C_6H_{14}NO_7P_2$) | | | |
|---|---|---|---|
| | C (%) | H (%) | N (%) |
| Calculated: | 26.19 | 5.50 | 5.09 |
| Found: | 25.94 | 5.27 | 5.11 |

(ii) m.p. (°C.) 247 to 251 (decomposition) (recrystallized from water-methanol)

EXAMPLE 14

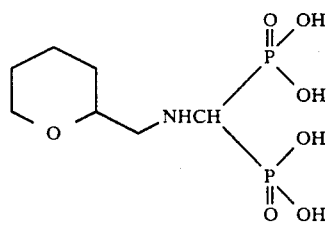

(Tetrahydropyran-2-yl-methyl)-aminomethylenebis(phosphonic acid)

(i) m.p. (°C.) 237 to 240 (decomposition) (recrystallized from water-acetone)

| (ii) Elemental Analysis (as $C_7H_{17}NO_7P_2$) | | | | |
|---|---|---|---|---|
| | C (%) | H (%) | N (%) | P (%) |
| Calculated: | 29.08 | 5.93 | 4.84 | 21.42 |
| Found: | 28.76 | 5.73 | 4.87 | 21.32 |

EXAMPLE 15

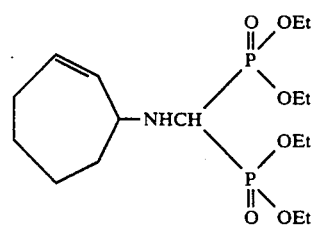

A mixture solution of 6.0 g of 2-cycloheptenylamine, 10.0 g of ethyl orthoformate and 37.3 g of diethylphosphite was heated at 150° C. under stirring for 3 hours. After cooling, the reaction solution was concentrated under reduced pressure to eliminate ethyl orthoformate and diethylphosphite which were not reacted. The obtained residue was purified on a silica gel column chromatography (methanol/chloroform=1/99) to give 11.7 g of tetraethyl(2-cycloheptenyl)aminomethylenebis(phosphonate) as a yellow oil.

The physico-chemical properties of this product are as follows:

(i) Mass Spectrum (m/z) FAB Mass): 398 (M+ +1)

| (ii) Nuclear Magnetic Resonance Spectrum (δ value, in CDCl₃) | |
|---|---|
| 1.32 | (12H, OCH$_2$C$\underline{H}_3$ × 4) |
| 1.22~2.40 | (9H, H in methylene in cycloheptenyl group, —NHC$\underline{H}$—) |
| 3.36 | (1H, —NHC$\underline{H}$—) |
| 3.68 | (1H, >C-N$\underline{H}$—) |
| 4.04~4.42 | (8H, —OC$\underline{H}_2$CH₃ × 4) |
| 5.52~5.96 | (2H, >C=C<, H H) |

In the same manner as Example 15, the following compounds were prepared.

EXAMPLE 16

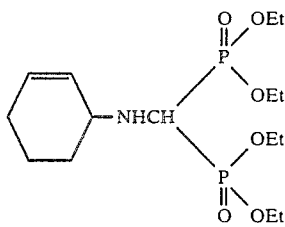

Tetraethyl(2-cyclohexenyl)aminomethylenebis(phosphonate)

(i) Mass Spectrum (m/z)(FAB Mass) 384 (M+1)

| (ii) Nuclear Magnetic Resonance Spectrum (δ value, in CDCl₃) | |
|---|---|
| 1.24~1.44 | (12H, t, —OCH$_2$C$\underline{H}_3$) |
| 1.48~2.08 | (6H, m, cyclic C$\underline{H}_2$) |
| 3.42 | (1H, t, —NHC$\underline{H}$, J=22 cps) |
| 3.48 | (1H, cyclohexyl NH—, $\underline{H}$) |
| 4.04~4.40 | (8H, m, —OC$\underline{H}_2$CH₃) |
| 5.56~5.88 | (2H, m, aryl C$\underline{H}$) |

EXAMPLE 17

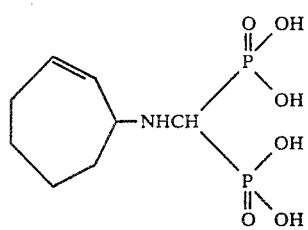

2.5 ml of trimethylsililiodide was added dropwise to an ice-cold solution of 1.55 g of tetraethyl(2-cycloheptenyl)aminomethylene-bis(phosphonate) in 25 ml of carbon tetrachloride. Then, the mixture was stirred at room temperature for 2.5 hours. 2 ml of methanol and 1 ml of purified water were added to the ice-cold reaction solution and it was concentrated under reduced pressure. To the obtained residue were added methanol and acetone to give a white solid. The residue was recrystallized from water-methanol to give 0.39 g of (2-cycloheptenyl)aminomethylenebis(phosphonic acid) as colorless crystals in the form of needles.

The physico-chemical characteristics of this product are as follows:

(i) m.p. (°C.) 230 to 233

| (ii) Elemental Analysis (as C₈H₁₇NO₆P₂) | | | | |
|---|---|---|---|---|
| | C (%) | H (%) | N (%) | P (%) |
| Calculated: | 33.69 | 6.01 | 4.91 | 21.72 |
| Found: | 33.52 | 5.78 | 4.84 | 21.86 |

In the same manner as Example 17, the following compounds were prepared.

EXAMPLE 18

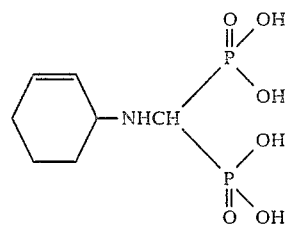

(2-Cyclohexenyl)aminomethylenebis(phosphonic acid)

(i) m.p. (°C.) 228 to 230 (decomposition)

| (ii) Elemental Analysis (as C₇H₁₅NO₆P₂) | | | | |
|---|---|---|---|---|
| | C (%) | H (%) | N (%) | P (%) |
| Calculated: | 31.01 | 5.58 | 5.17 | 22.85 |
| Found: | 30.82 | 5.46 | 5.00 | 22.58 |

PRESCRIPTION EXAMPLE

Examples for prescription of the compounds of the present invention as a drug will be mentioned below.

| Tablet (a): | |
|---|---|
| Compound of Example 3 | 5 mg |
| Lactose | 119 mg |
| Corn Starch | 67 mg |
| Hydroxypropyl Cellulose | 4 mg |
| Carboxymethyl Cellulose Calcium | 4 mg |
| Magnesium Stearate | 1 mg |
| Total | 200 mg |

5 g of the compound of Example 3, 119 g of lactose and 67 g of corn starch were uniformly blended, 40 ml of an aqueous solution (10% w/w) of hydroxypropyl cellulose was added thereto, and the resulting mixture was granulated in wet. The granules thus obtained were blended with 4 g of carboxymethyl cellulose calcium and 1 g of magnesium stearate, and the resulting mixture is shaped into tablets each having a weight of 200 mg/tablet.

Tablet (b)

The same operation as above was repeated except that 5 g of the compound of Example 13 was used instead of 5 g of the compound of Example 3 in the prescription to obtain tablets each having a weight of 200 mg/tablet.

| Capsule (a): | |
|---|---|
| Compound of Example 3 | 5 mg |
| Crystalline Cellulose | 50 mg |
| Crystalline lactose | 144 mg |
| Magnesium Stearate | 1 mg |
| Total | 200 mg |

The above-mentioned ingredients were blended each in an amount of 1,000 times of the above-mentioned amount and encapsulant in gelatin capsules so that one capsule contains 200 mg of the mixture.

Capsule (b)

The same operation as above was repeated except that 5 g of the compound of Example 13 was used instead of 5 g of the compound of Example 3 in the prescription to prepare capsules each has a weight of 200 mg/capsule.

We claim:

1. A pharmaceutical composition comprising a substituted aminomethylenebis(phosphonic acid) derivative represented by the general formula:

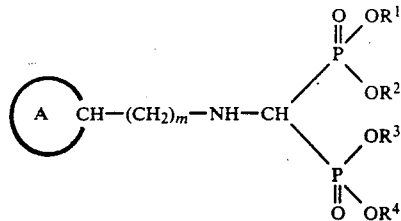

in which $R^1$, $R^2$, $R^3$ and $R^4$ may be the same or different, each represents a hydrogen atom or a lower alkyl group; "m" is zero or represents an integer from 1 to 4; and ring "A" represents a cycloalkenyl group having 5 to 8 carbon atoms, a bicycloheptyl group, a bicycloheptenyl group or a saturated heterocyclic group having 4 to 7 carbon atoms and containing at least one member selected from the group consisting of an oxygen atom, a sulfur atom, a sulfinyl group (—SO—) and a sulfonyl group (—SO$_2$—), or pharmaceutically acceptable salts thereof and a pharmaceutically acceptable carrier.

2. The pharmaceutical composition claimed in claim 1, wherein the substituted aminomethylenebis(phosphonic acid) derivative is (2,3,4,5-tetrahydro-2-furfuryl-)aminomethylene-bis(phosphonic acid).

3. The pharmaceutical composition claimed in claim 1, wherein the substituted aminomethylenebis(phosphonic acid) derivative is (2-bicyclo[2.2.1]-heptyl-)aminomethylene-bis(phosphonic acid).

4. The pharmaceutical composition claimed in claim 1, wherein the substituted aminomethylenebis(phosphonic acid) derivative is (2-cycloheptenyl)aminomethylenebis(phosphonic acid).

* * * * *